United States Patent
Bettles

(10) Patent No.: US 9,433,806 B2
(45) Date of Patent: Sep. 6, 2016

(54) PROSTHETIC APPLIANCE KIT

(71) Applicant: Stephen Bettles, Los Angeles, CA (US)

(72) Inventor: Stephen Bettles, Los Angeles, CA (US)

( * ) Notice: Subject to any disclaimer, the term of this patent is extended or adjusted under 35 U.S.C. 154(b) by 0 days.

(21) Appl. No.: 14/574,065

(22) Filed: Dec. 17, 2014

(65) Prior Publication Data

US 2016/0175621 A1    Jun. 23, 2016

(51) Int. Cl.
*A61Q 90/00* (2009.01)
*B29C 43/00* (2006.01)

(52) U.S. Cl.
CPC ............. *A61Q 90/00* (2013.01); *B29C 43/006* (2013.01); *B29K 2003/00* (2013.01); *B29K 2005/00* (2013.01)

(58) Field of Classification Search
CPC ................................ A61Q 90/00; A63B 69/36
See application file for complete search history.

(56) References Cited

U.S. PATENT DOCUMENTS

| | | | |
|---|---|---|---|
| 4,268,468 A | 5/1981 | Esper et al. | |
| 8,308,817 B2 | 11/2012 | Egilsson et al. | |
| 8,403,766 B2 | 3/2013 | Tinsley | |
| 2004/0137178 A1 | 7/2004 | Janusson et al. | |
| 2010/0155288 A1 | 6/2010 | Harpet et al. | |
| 2012/0261296 A1* | 10/2012 | Tinsley | B29C 39/10 206/461 |
| 2013/0309643 A1* | 11/2013 | Segall | G09B 23/303 434/268 |

* cited by examiner

*Primary Examiner* — Michael Dennis
(74) *Attorney, Agent, or Firm* — Sanford Astor; Brooks Kushman P.C.

(57) ABSTRACT

Prosthetics created in layers, and methods of making them, comprising one or more materials. The methods utilize a clay sculpture from which is made a negative impression cast in silicone, which is used to cast a durable positive prosthetic, which is used to create either durable or temporary negative production impressions into which the layers can be built to form the finished prosthetic.

9 Claims, 15 Drawing Sheets

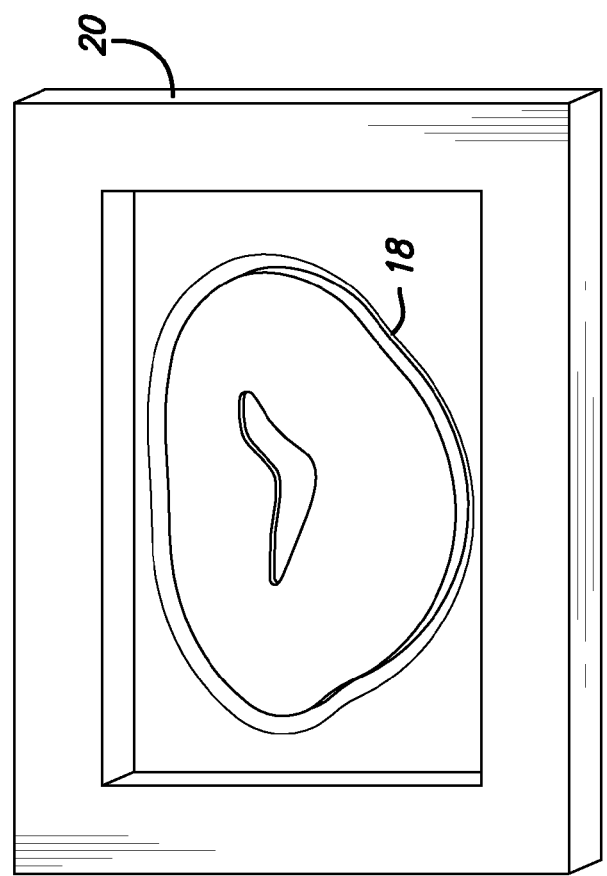
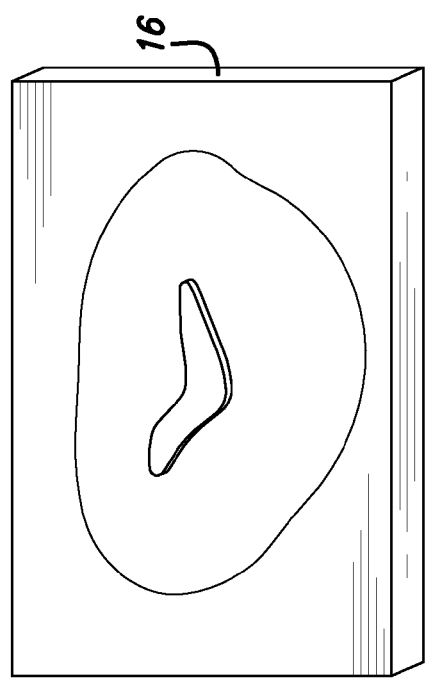
FIG. 5

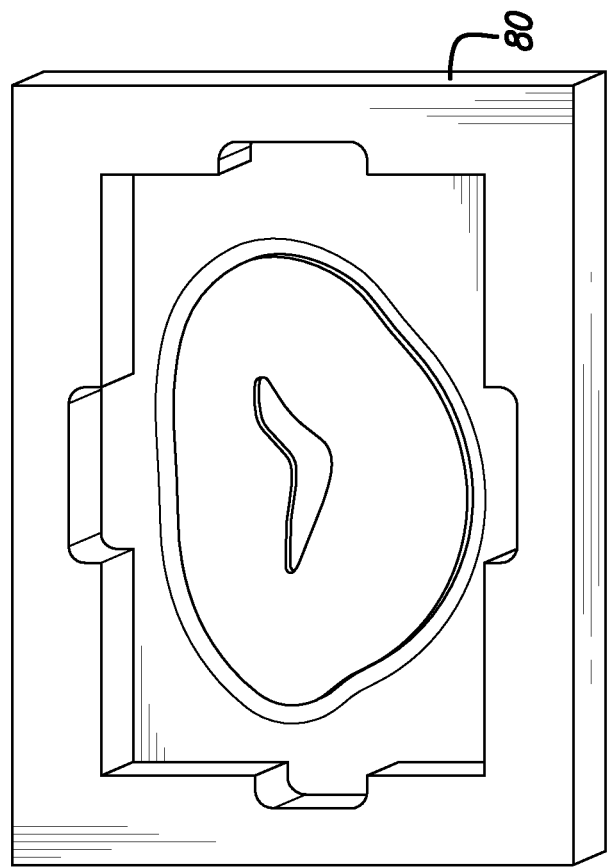
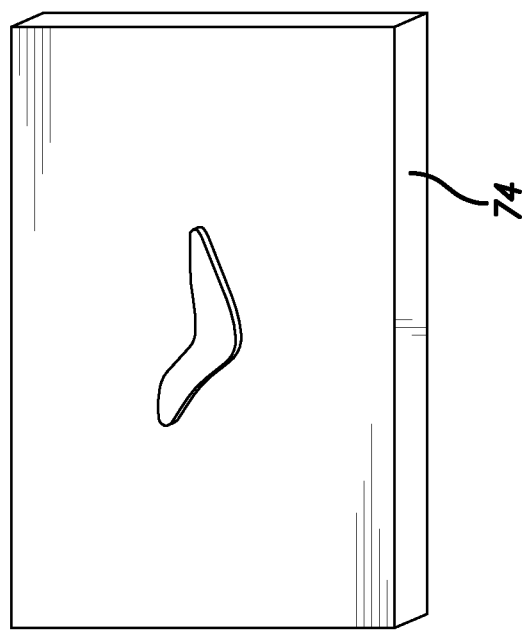
FIG. 6

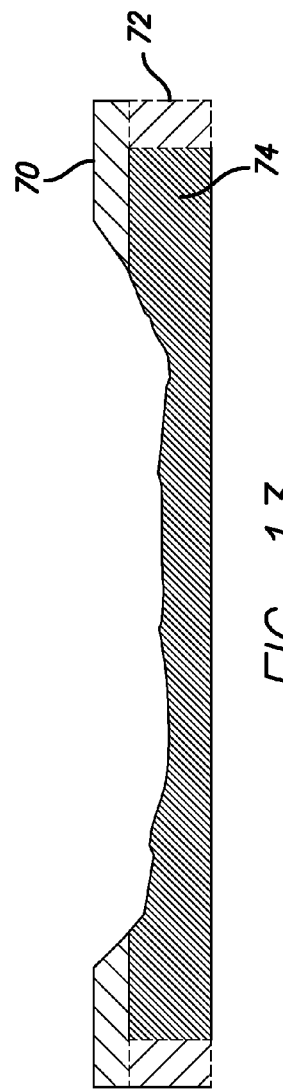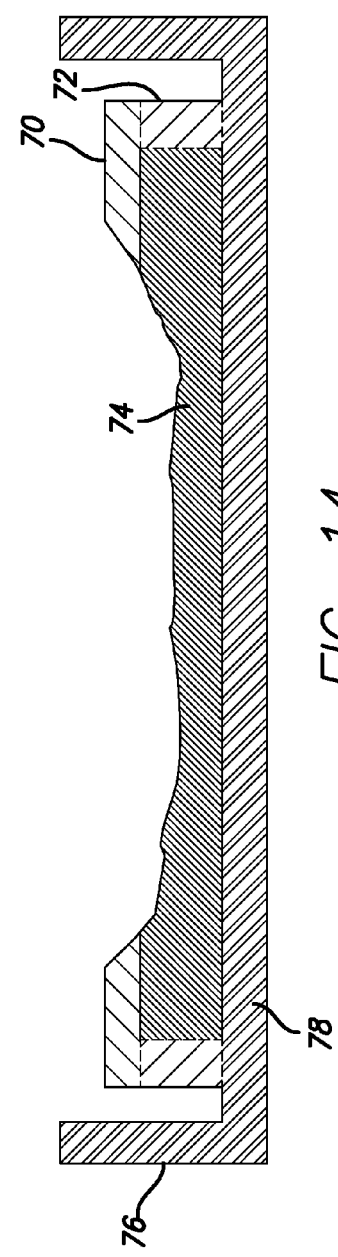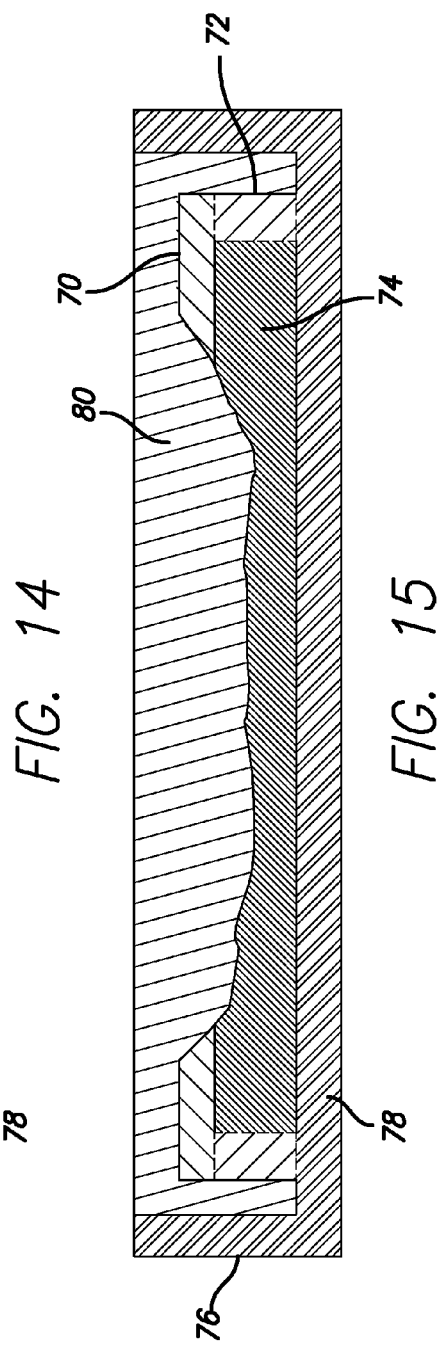

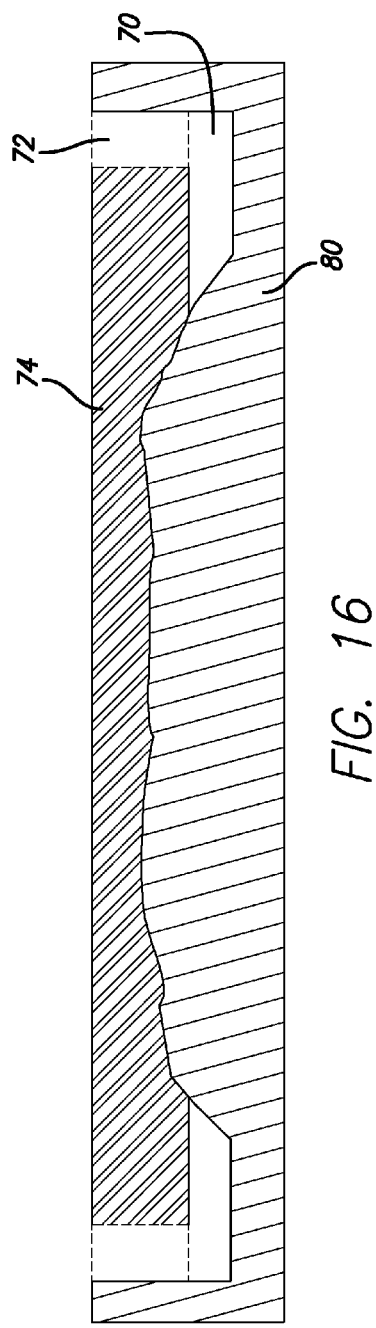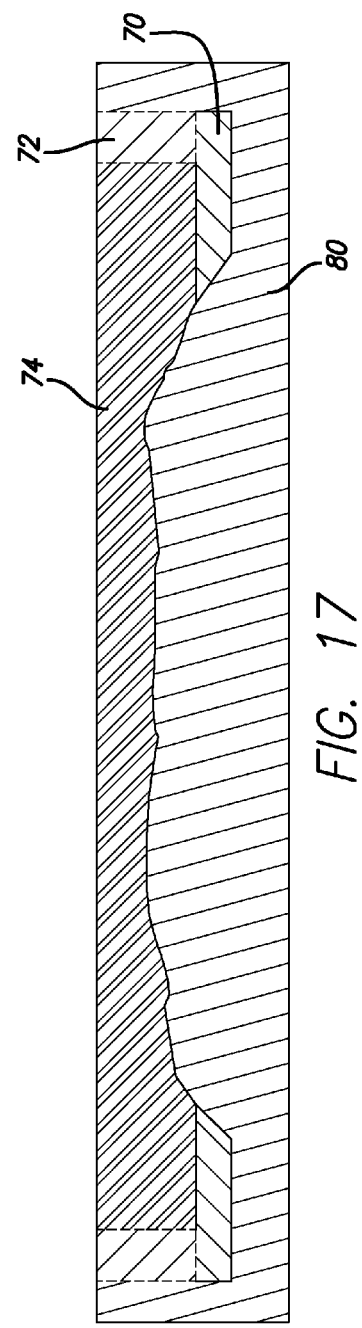

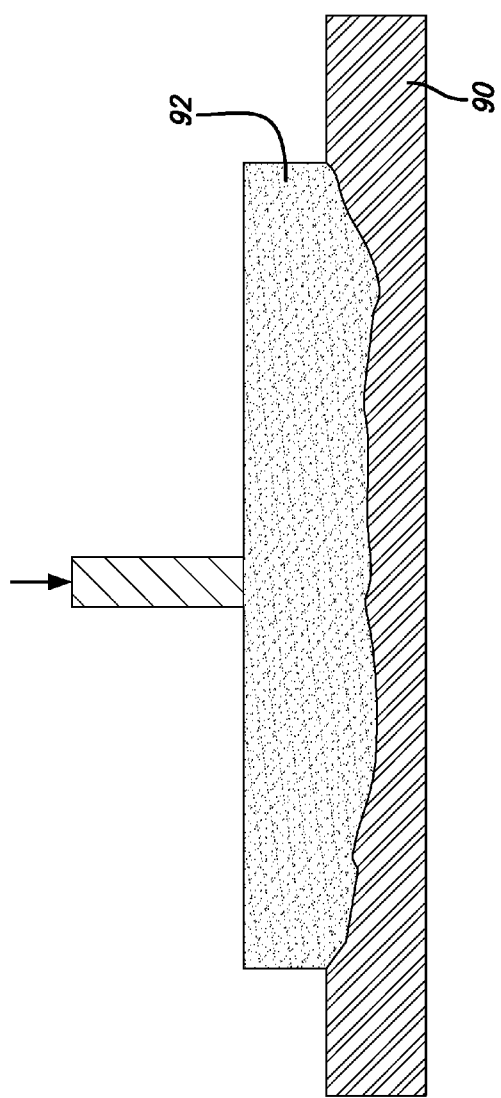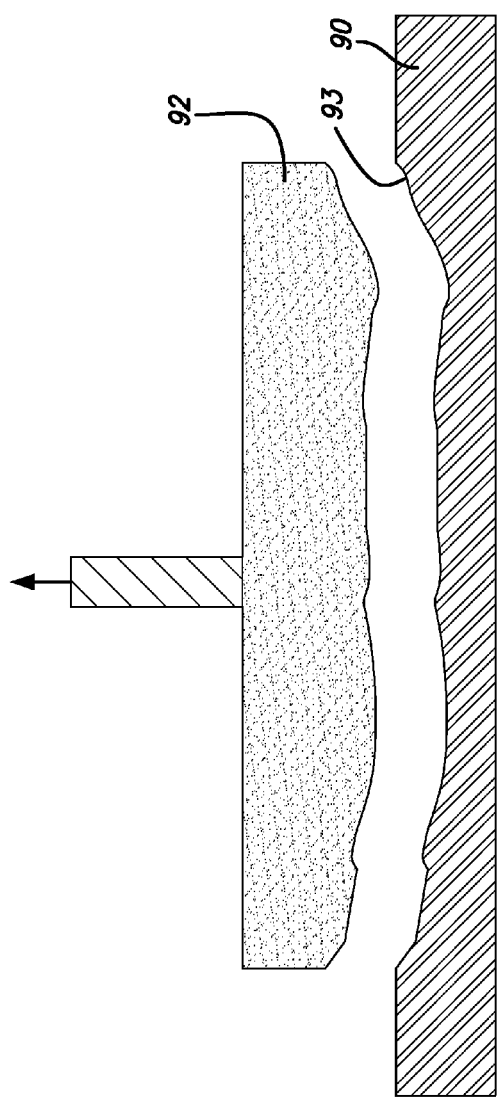

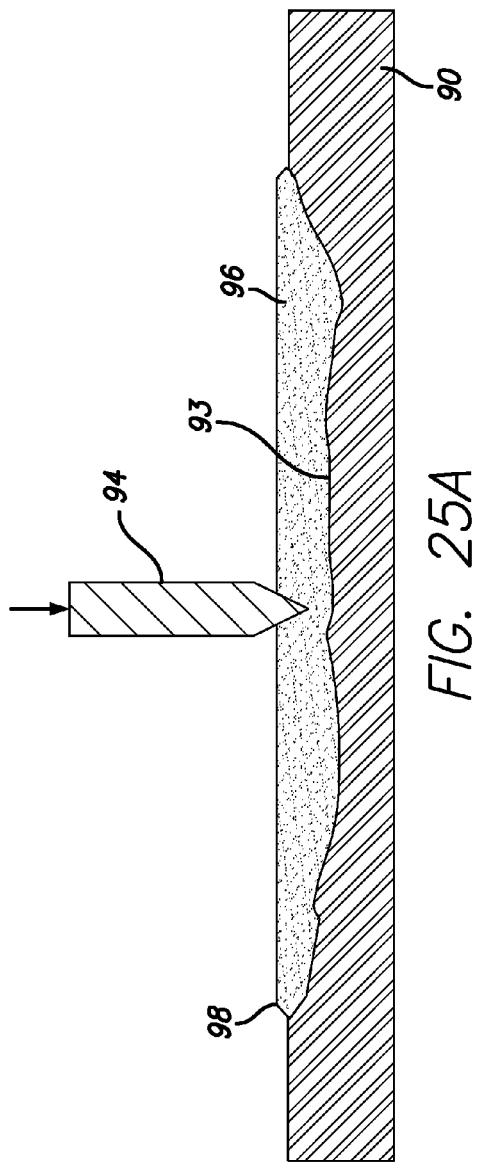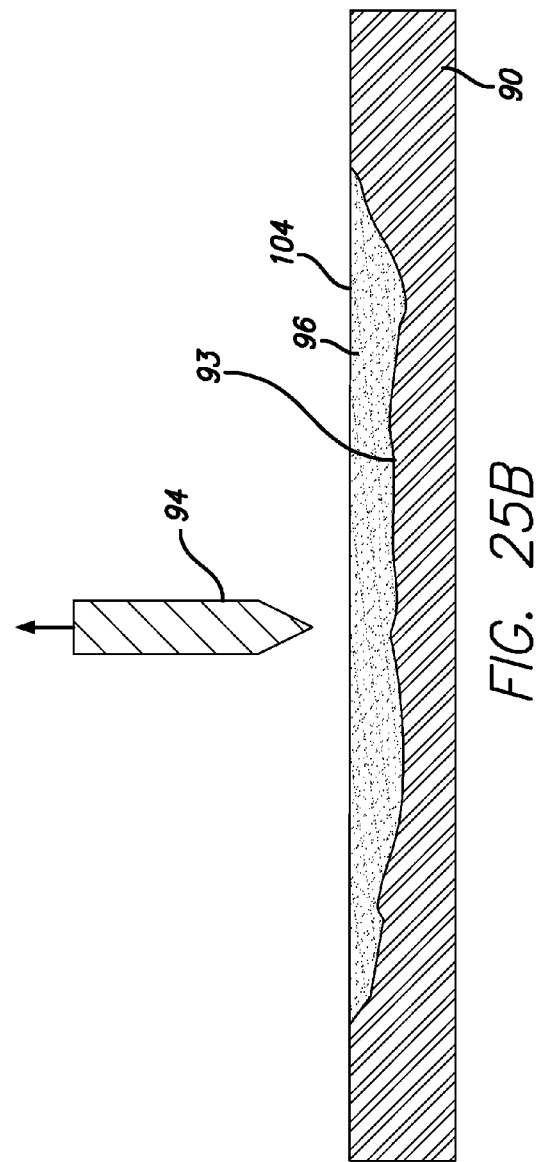

PROSTHETIC APPLIANCE KIT

TECHNICAL FIELD

This invention comprises producing a new prosthetic appliance and a prosthetic appliance kit to create prosthetic appliances for use by make-up artists in the entertainment field, as well as other persons.

BACKGROUND

Prosthetic appliances are used by make-up artists who create special effects for films, television, stage, etc. The prosthetic appliances are also used by other persons, for instance at Halloween. The prosthetic appliances are used to simulate realistic injuries, deformities, and other unusual features on a person's face or body. The process that has previously been used involves creating a prosthetic appliance and later transferring the appliance to a person, such as an actor. Make-up must be applied to complete the process. This method takes too much time and requires additional procedures to complete the process. In U.S. Pat. No. 8,403,766 issued Mar. 26, 2013, Christien Tinsley, disclosed a method of transferring of a prosthetic appliance to the skin of a wearer. His kit includes a first and second transfer portions which may be provided in combined form. The first transfer portion includes a prosthetic appliance and a release film. The second transfer portion includes a transfer substrate, an adhesive layer and a release coat therebetween. Tinsley has a two-step method of application. Water slide paper has to be applied to the surface of the prosthetic appliance. The one-piece peel-able release film is thereby removed exposing the back of the appliance. The back of the appliance is then applied to the skin and pressed firmly. Using a damp sponge, water is applied to the surface of the paper activating the release underneath allowing the paper to be peeled off of the appliance, leaving it on the skin. In addition, Tinsley's prosthetics are made solely of thickened adhesive material scraped into a negative mold. The adhesive is a pressure sensitive skin safe acrylic. Once applied to the skin the surface of the prosthetic remains sticky until sealed with make-up. The method of Tinsley takes too much time to apply and the prosthetic remains sticky until sealed with make-up. Applicant's method is much faster to apply, is not sticky and does not require make-up after it is applied.

SUMMARY

Applicant's method uses a unique one-step application. The back of the prosthetic uses two pieces of release film which slightly overlap each other and cover an adhesive layer. To apply, you simply remove the first piece of the release film, apply the prosthetic to the skin, then remove the second piece of release film and press firmly, leaving the appliance attached to the skin.

To avoid or minimize the use of make-up, the prosthetics are self-colored to match the skin and have a non-sticky outer surface. All the construction methods and manufacturing processes described herein achieve these aims by utilizing a pigmented platinum silicone within the main body of the prosthetic structure to achieve a match to the wearer's skin tone and a non-sticky coating on the front surface of the prosthetic.

Controlled adhesion of the prosthetic to the wearer's skin and easy removal of the release films from the prosthetic are important to ensure ease of application. The construction and manufacturing methods described herein achieve this either by the uniform edge to edge application of a skin safe adhesive to the back of the prosthetic or by control of the natural high adhesion provided by the silicone molding material used within the construction by partial surface coating.

To ensure a realistic appearance, the thickness of the prosthetic edge is minimized to ensure a smooth and invisible transition between the prosthetic and the wearer's skin. Manufacturing methods for control of edge thickness are described herein, including use of a spray guard to define and 'feather' the outer edge of the prosthetic and controlled volume reduction when molding to minimize the casting meniscus at the edge of the product.

Applicant's prosthetics are created in layers using several different materials. Several alternative constructions are described. All the methods utilize a handcrafted clay sculpture of the desired prosthetic as a starting point, and from this, a negative impression is cast in silicone. This negative impression is then used to cast a durable positive prosthetic, which in turn is used to create either durable or temporary negative production impressions into which the layers of the prosthetic can be built up to form the finished product.

The developments described herein allow the user to create advanced looking prosthetic make-up effects in a fraction of the time of present methods, without the need for all of the traditional methods of construction and application.

BRIEF DESCRIPTION OF THE DRAWINGS

FIG. 5 is a top view of the master negative and a positive copy of the master used to produce all the production molds;

FIG. 6 is a top view of the negative mold and the spray guard mold;

FIG. 13 shows step one of the construction sequence for a spray guard mold;

FIG. 14 shows step two of the construction sequence for a spray guard mold;

FIG. 15 shows step three of the construction sequence for a spray guard mold;

FIG. 16 shows step four of the construction sequence for a spray guard mold;

FIG. 17 shows use of the completed mold to cast a spray guard;

FIGS. 24A and 24B show sectional views of step two for a two layer powder molding process for prosthetics;

FIGS. 25A and 25B show sectional views of step three for a two layer powder molding process for prosthetics;

DETAILED DESCRIPTION

Figure 1:
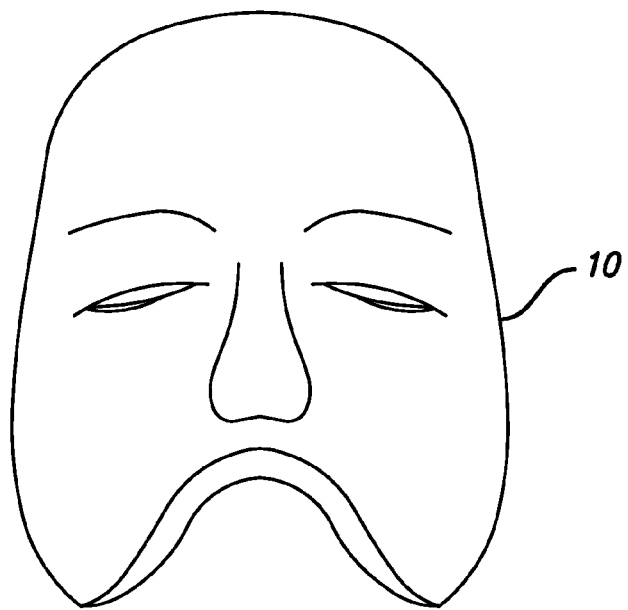
FIG. 1 is a front view of a plaster cast.
Figure 2:
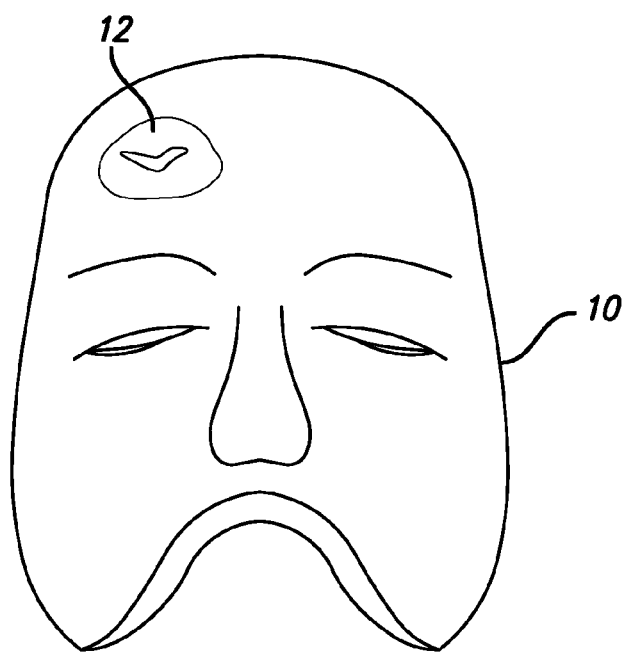
FIG. 2 is a front view of the plaster cast of FIG. 1, with a sculpt applied.
Figure 3:
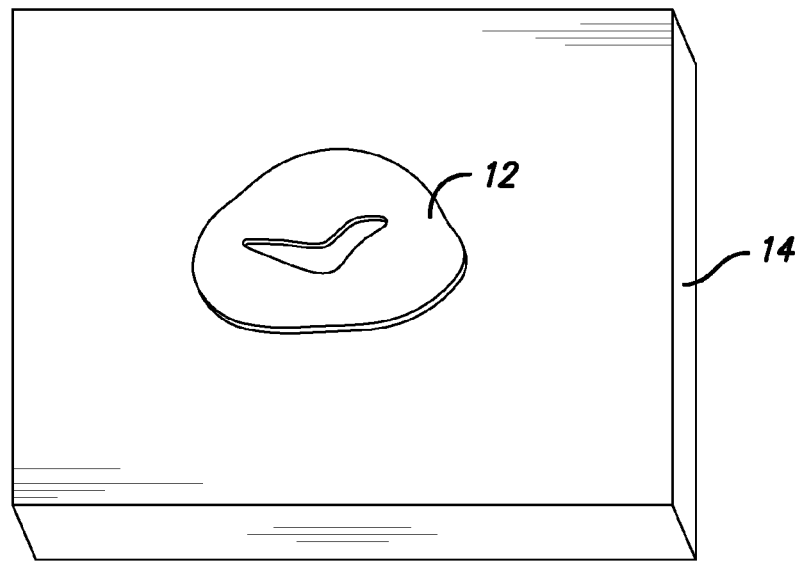
FIG. 3 is a front view of the detailed sculpt on a flat board.
Figure 4:
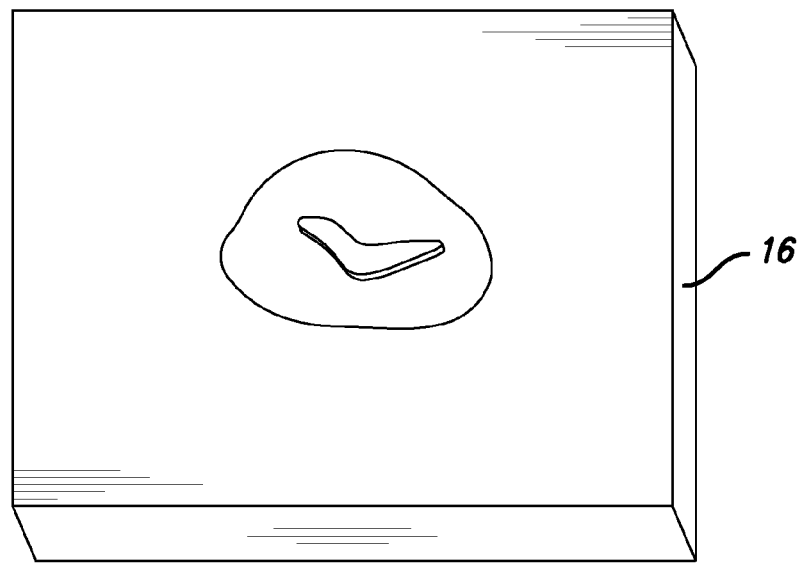
FIG. 4 is a top view of a master negative prosthetic.

Referring now to the drawings, FIGS. 1 through 5, a plaster cast 10 is painted with a water based paint which is the same color as the clay that will be used to sculpt the prosthetic. The plaster cast can be a generic cast or, if desired, cast from a specific person, such as an actor. Then, one or more layers of a separating agent, such as Alcote, are applied to the cast 10, which later allows a sculpt to float off of the cast.

Then, a sculpt 12 is created out of a soft clay, such as a sulpha free soft chavant clay, although many other clays can be used, onto plaster cast 10. Once the sculpt 12 is completed, the cast 10 is placed in water to float off the sculpt 12. The sculpt 12 is then placed on a flat board 14 and is detailed and smoothed if needed, see FIG. 3. The sculpt 12 is then sprayed with one or more layers of an acrylic or lacquer, such as Krylon Crystal Clear, optionally followed by one or more layers of a dulling spray, such as Krylon and a mold release, such as Ease Release 300.

The sculpt 12 is then surrounded by a casting box with walls, which are made of clay, wood, or other material and the walls are sealed, or pre-sealed together by glue, or any other adhesive, to hold the walls in place. Then, a liquid silicone is poured into the box. The liquid silicon, such as Mold Star 16 fast, or other similar silicone materials, solidifies and there is left a master negative prosthetic 16, see FIG. 4.

The master negative prosthetic 16 is again surrounded by a casting box having an annular gap and the prosthetic piece 16 is sprayed by a mold release over the entire surface and then a silicone, like Mold Star 16, is poured over the entire piece and into the annular gap. This leaves a mold 18, which is a positive copy of the master negative prosthetic having an integral casting box wall 20 around it which is used to produce all the production molds for making prosthetic pieces, see FIG. 5.

Mold 18 is then sprayed with a mold release and is filled with a liquid thermo-set plastic, such as a resin or fiberglass, which hardens to a hard plastic version 74 of the negative mold 16, see FIG. 6. Manufacture of a hard durable plastic version of the negative mold for use in production manufacturing is unique, due to the need to produce large quantities of prosthetic appliances.

Figure 18A:
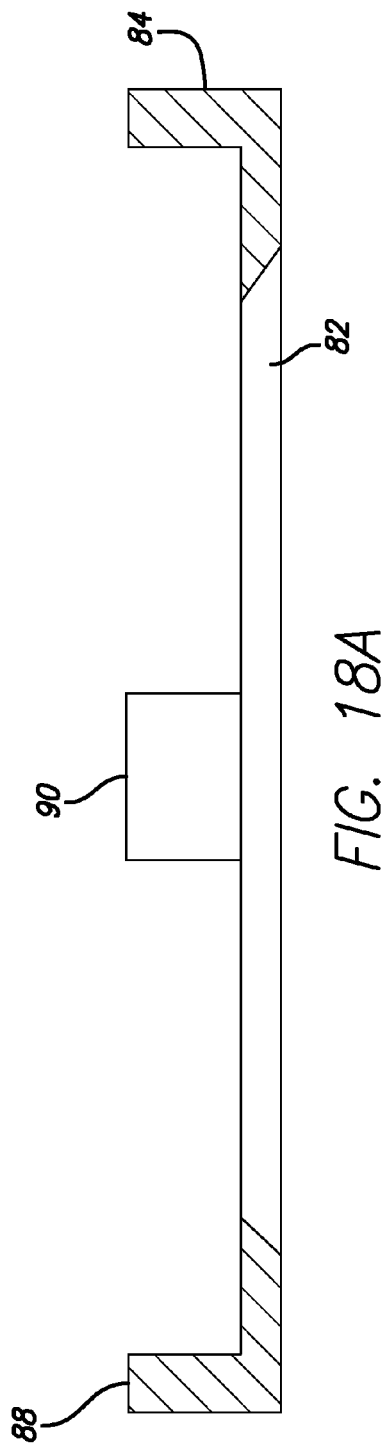
FIGS. 18A and 18B show the de-molded finished cast spray guard.
Figure 18B:
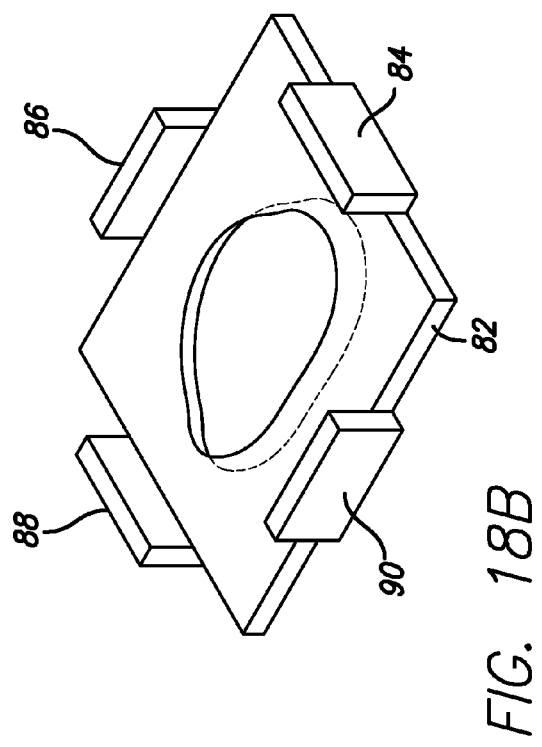

FIGS. 6 and 13-17 show the steps in the construction of a mold 80 to cast a spray guard 82 and FIGS. 18A and 18B show the finished cast spray guard 82.

FIG. 13 shows a section through a prosthetic mold for step one of the construction sequence for a spray guard mold 80. A clay sculpt of the spray guard 82 comprising upper surface 70 and location nibs 72 is added to a negative mold of the prosthetic 74. The downward location nibs of the sculpt are only local to the center of each side of the negative mold of the prosthetic 74.

FIG. 14 shows step two in which walls 76 and 78 are created to form a temporary casting box for the negative spray guard mold 80.

FIG. 15 shows step three, in which after spraying the negative mold of the prosthetic 74 and clay sculpt, comprising 70 and 72, with release agent, the spray guard mold 80 is cast using a silicone, such as Mold star 16 fast silicone.

FIG. 16 shows step four in which the clay sculpt 70, 72 has been removed from the spray guard mold 80 and negative prosthetic mold 74. The two components 74 and 80 are then reassembled after spraying with mold release and inverted, ready to cast a positive mold of a spray guard in the void left by the removal of the clay sculpt of the spray guard 70 and 72. The two components of the mold, items 74 and 80, are shown ready to assemble for casting, in FIG. 6.

FIG. 17 shows step five, the casting of a spray guard 82. The void left by removal of the clay sculpt 70, 72 is filled with a polymer, such as Onyx fast cast which is a hard plastic or an elastomer such as silicone rubber. FIG. 18A shows a section through a completed prosthetic spray guard 82, and FIG. 18B shows a perspective view of the completed prosthetic spray guard 82, with location lugs 84, 86, 88 and 90.

Spray guard 82 is a key step in the process. Spray guard 82 allows the application of an encapsulation layer into the mold, which has never before been done, which keeps the surface of the prosthetic piece from being tacky. It also allows the control of where each layer in the process is applied, so that one layer does not extend beyond another layer, defining the edge of the prosthetic, ensuring that the best quality prosthetic is made.

The end result is thinner edges, which are key when blending into the skin of a performer. Also, by having a skin safe plastic encapsulation cover layer, glue can be applied to the very edge of a prosthetic piece so that total adhesion of the prosthetic piece to the skin is possible.

To produce a new prosthetic out of the negative mold 74, using spray guard 82, the structure and procedure is as described below. See FIGS. 9 and 19-22.

Figure 9:
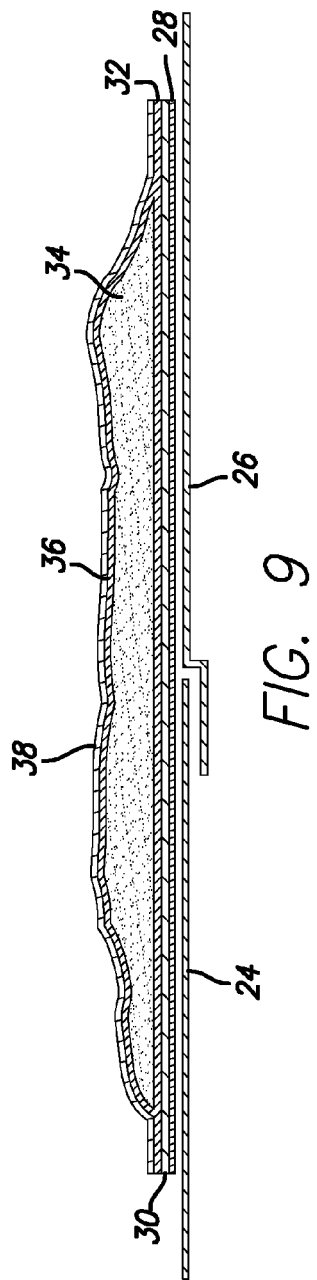
FIG. 9 shows a section view of the finished prosthetic.

FIG. 9 shows a section through the complete prosthetic showing the structure. Described from the bottom layer up, FIG. 9 shows the coated release film of paper, plastic or metallic foil, 24 and 26, a pressure sensitive adhesive layer 28, such as Pros-aid, a skin safe plastic encapsulation cover layer 30, such as Baldiez, an adhesive layer 32, such as 3M Spray Mount, a platinum silicone prosthetic material 34, another adhesive layer 36, and another layer of skin safe plastic encapsulation cover layer 38.

The fewer the layers the less quality is obtained. Simply put, the difference between a 1-layer system and 7-layer system is quality of detail, thickness of the edge, and adhesion strength. In a 7-layer system, each of the layers has a specific purpose.

Figure 19:
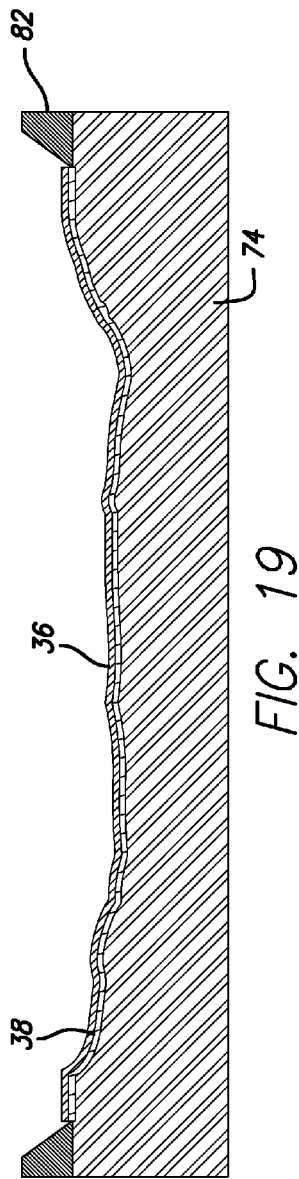
FIG. 19 shows a sectional view of step one of the prosthetic construction sequence.

FIG. 19 shows a section through the prosthetic illustrating step one in the construction sequence. The negative mold 74 is sprayed with one or more layers of release spray, such as epoxy parafilm ultra 4 release spray. The spray guard 82 is placed over the negative mold 74.

Then, step one is the first layer which is formed by 1 to 20 coats of skin safe plastic encapsulation cover 38, such as Baldiez, sprayed on top of the negative mold. This layer prevents the surface of the prosthetic appliance from being sticky by acting as an encapsulate.

Then, step two is a layer 36, of adhesive, such as 3M Spray Mount is the sprayed as the second layer. This helps bind the first and the third layers so they do not delaminate when de-molding or applying and removing the prosthetic from the actor's skin.

Figure 7:
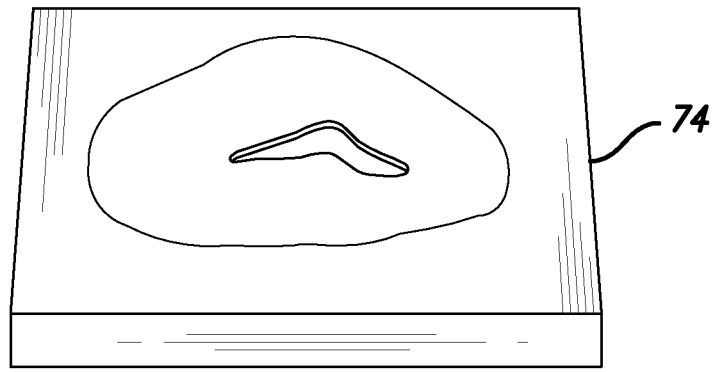
FIG. 7 is a top view of a production mold filled with tinted silicone.
Figure 20:
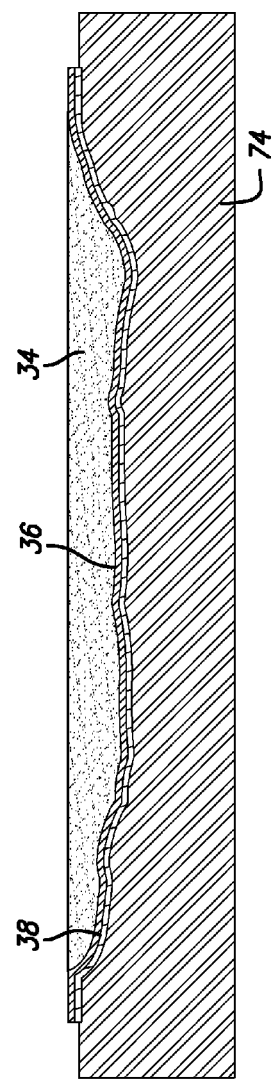
FIG. 20 shows a sectional view of step two of the prosthetic construction sequence.

FIG. 20, shows step three in the construction sequence in which the negative mold 74, has the spray guard 82 removed and the cavity of the negative mold, which is coated with skin safe plastic encapsulation cover layer (cap) 38, and the adhesive layer 36, is filled with the third layer, a tinted softened platinum silicone prosthetic material 34, such as Platgel10 with a deadener, such as Polytek Gordon Smith, which softens the silicone and pigment to tint. FIG. 7 shows a top view of the negative mold 74. This is the bulk of the appliance, filling the mold and creating the desired color. It is softened to achieve a more realistic fleshy look. This material, although sticky, has a stronger adhesion to the encapsulation plastic when used in conjunction with adhesive layers. The excess is scraped off using a metal plaster scraper, or any other similar tool and the edges are then cleaned using a cleanser such as alcohol and paper towels or other similar cleaners.

Figure 21:
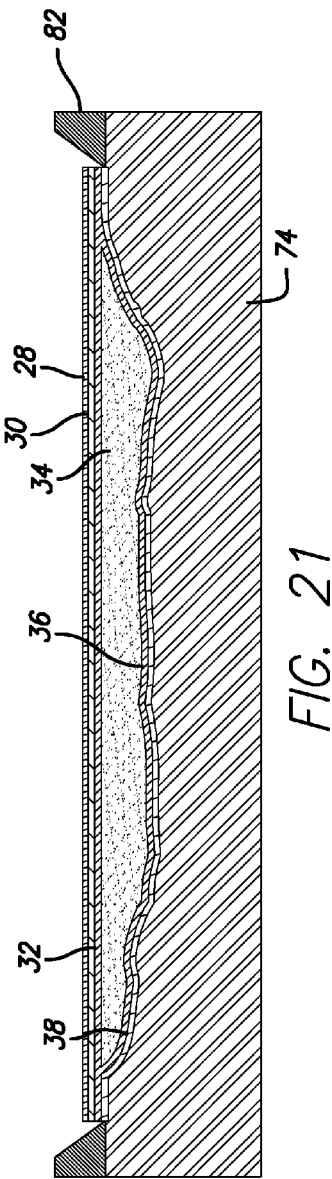
FIG. 21 shows a sectional view of step three of the prosthetic construction sequence.

FIG. 21 shows step four in the construction sequence in which the negative mold 74, has had the spray guard 82 replaced and then the previous layers described above are sprayed with another adhesive layer, 32, such as 3M Spray Mount.

Step five comprises adding another layer of skin safe plastic encapsulation cover layer 30. To achieve realistic looking prosthetics, the silicone has to be softened to the point where it would not release from the release film used, hence the need for additional encapsulation.

The sixth step is adding a layer of pressure sensitive skin safe adhesive layer 28, such as Pros-aid. This layer allows the attachment of the prosthetic piece to the skin and yet allows it to easily release from the release film.

Figure 8:
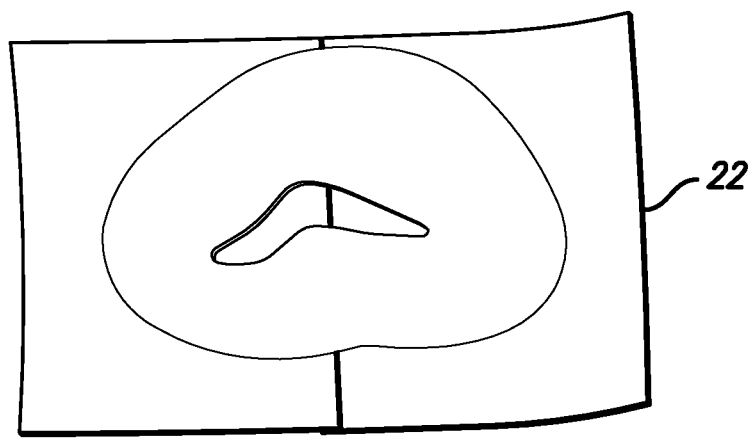
FIG. 8 is a top view of the finished prosthetic piece.
Figure 22:
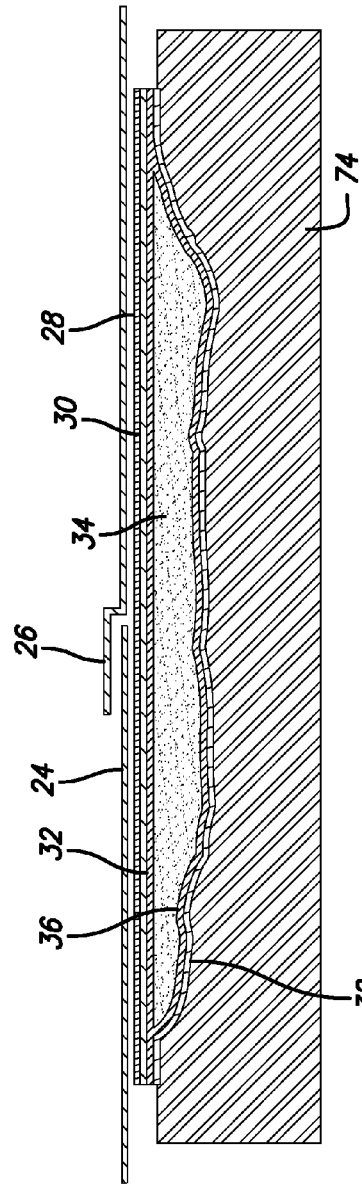
FIG. 22 shows a sectional view of step four of the prosthetic construction sequence.

FIG. 22 shows step seven in the construction sequence in which the negative mold 74, again has the spray guard 82 removed. Once the spray guard 82 is removed and the adhesive has dried, there is placed over one-half of the prosthetic piece, 22, a piece of release film 24, made of paper, plastic or metallic foil, such as aluminum. Another piece of release film, of paper, plastic or metallic foil 26 is placed over the second half of the prosthetic piece, slightly overlapping the first piece 24, both release films 24 and 26 are laid onto the sixth adhesive layer. Then the whole prosthetic piece, 22, can be peeled out of the negative mold, 74, still attached to the release films 24 and 26, which leaves the finished prosthetic piece ready for use, see FIG. 8, which shows the two release films, as described above. In addition, the release film can be coated with a cross linkable silicone, or other coatings, such as a low surface energy material, such as fluorocarbon plastics, such as PTFE. These optional coatings will make the release films less bondable, if needed, so that they will release easier.

In a 6-layer system each of the layers has the purpose set forth in the seven layer system except the adhesive layer between the first and third layer is left out, so that now the second layer is the silicone. The same final piece is created but it has a built in weakness of not binding strongly to the layer one encapsulate layer.

In a 5-layer system each of the layers has the purpose set forth in the 7-layer system except the adhesive layer between layer one and layer three, and layers 3 and 5, which are left out, so the same final piece is created but it has a built in weakness of not binding strongly to either one of the encapsulate layers.

Figure 11:
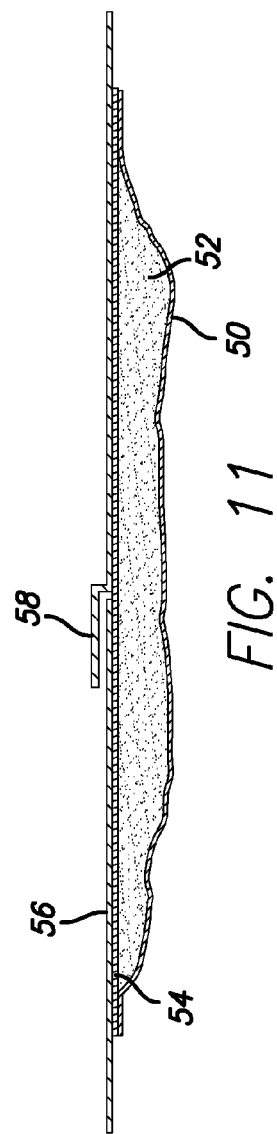
FIG. 11 shows an alternative four layer prosthetic.

FIG. 11 shows an alternative four layer prosthetic which comprises a skin safe plastic encapsulation cover layer 50, a platinum silicone prosthetic material 52 containing a deadener, pigment to tint, a pressure sensitive adhesive layer 54 and the release films 56 and 58. Leaving out both binding adhesive layers and the second skin safe plastic encapsulation layer, there is a weak bond between the first and second layers plus there is now the risk of the very sticky silicone 52 touching the release film 56, 58 through the pressure sensitive adhesive layer 54 and not releasing from the release film 56, 58 when it is time to be used.

Figure 10:
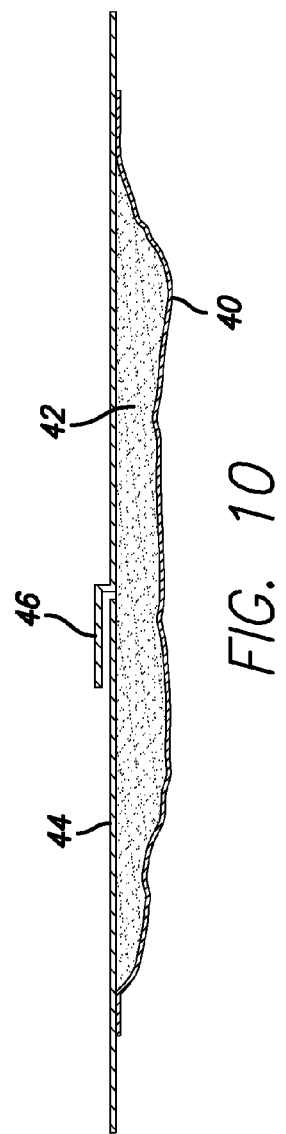
FIG. 10 shows an alternative three layer prosthetic.

FIG. 10 shows an alternative three layer prosthetic which contains a skin safe plastic encapsulation cover layer 40, a platinum silicone prosthetic material 42 containing a deadener, pigment to tint, and a partial surface coating to reduce "stickiness" of the silicone material, such as a powder or ink and the release film 44 and 46.

Figure 27:
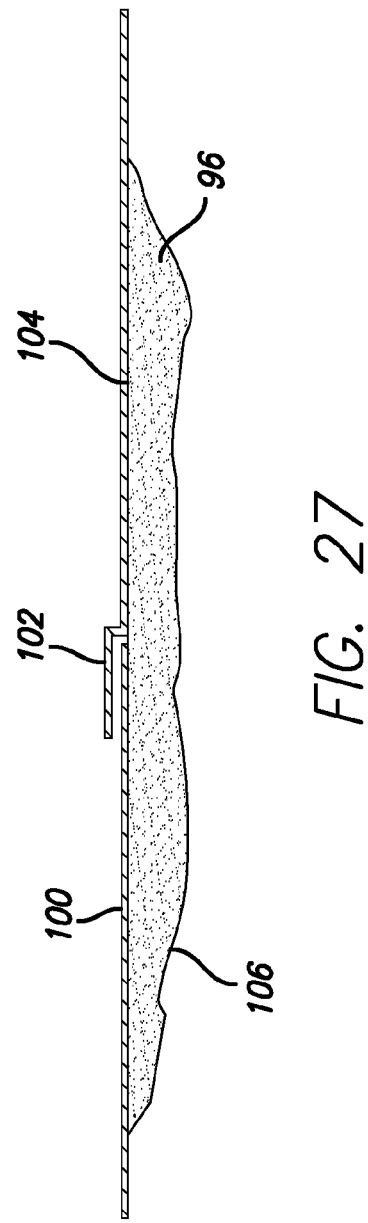

In a two layer system, shown in FIG. 27, the first layer is tinted softened silicone. This is the bulk of the appliance filling the mold and creating the desired color. It is softened to achieve a more realistic fleshy look. The outer surface of the prosthetic is rendered non-sticky by adhesion of powder from the mold to the surface of the platinum silicone. The second step is to partially blind the surface 104 by printing ink or powder in a pattern to partially cover the surface so that the prosthetic will still release from the release film. The third step is to apply the second layer which is two or more pieces of release film 100 and 102, laid onto the partially blinded silicone layer.

Figure 12A:
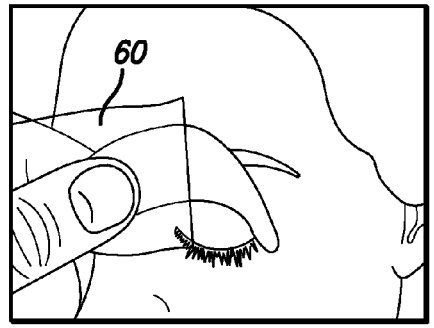
FIGS. 12A, 12B, 12C and 12D depict how to apply the prosthetic to the skin.
Figure 12B:
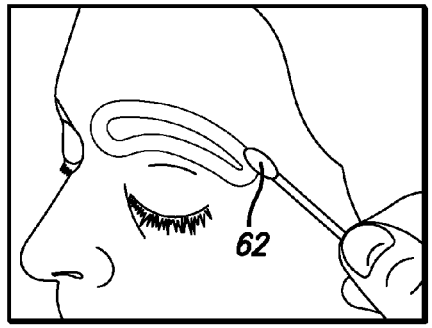
Figure 12C:
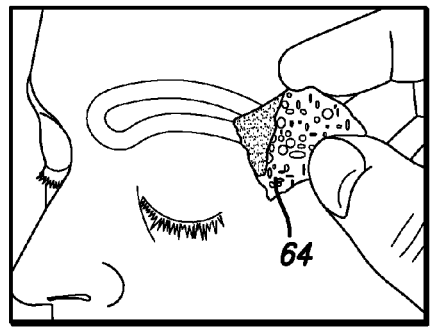
Figure 12D:

FIGS. 12A through 12D show how to use and apply the prosthetic when it has been removed from the packaging. Peel one release film from the prosthetic and apply to the skin. Then remove the second release film and complete the application. FIG. 12A shows one way of removal of the first half of the release film 60 and applying the prosthetic to the skin, pressing firmly down. FIG. 12B shows that, if desired, you can blend and smooth the prosthetic edge with a little acetone on a Q tip 62. Step 12C shows that some make-up 64 can be applied, again only if desired. FIG. 12D shows the finished product.

Figure 23:
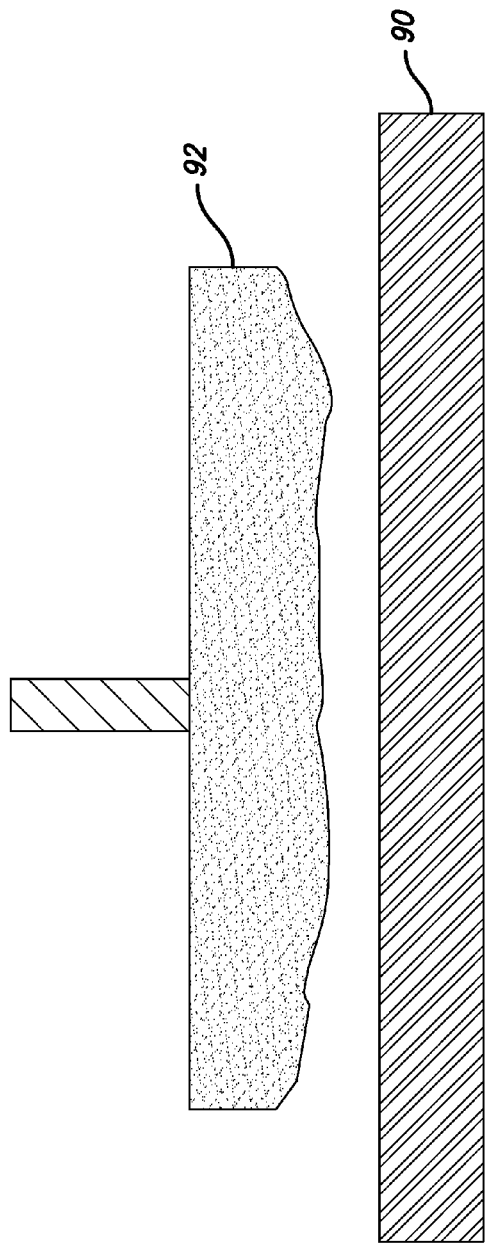
FIG. 23 shows a sectional view of step one for a two layer powder molding process for prosthetics.

FIG. 23 describes a two layer molding process for mass production of prosthetic products. There is a bed of powder, such as starch or lactose 90. A hard positive tool 92, shaped as a prosthetic, is mounted on a rigid platen with vertical movement to enable it to be pressed into the powder bed 90 to form a compacted impression. Tool 92 may be made of plastic or any other hard material.

FIG. 24A shows the hard tool 92 of a prosthetic on a rigid platen, which has vertical movement, is pressed tool down into the powder bed 90 to form a compacted impression of the prosthetic. FIG. 24B shows tool 92 returned to the up position leaving a compacted impression 93 formed in the surface of the powder bed 90.

FIG. 25A shows a dispensing device, 94 lowered into the impression 93 a distance below the finished surface of the prosthetic to dispense a pool of platinum silicone prosthetic material 96 with deadener and pigment to tint. Dispensing device 94 could be an auto pipette which is suitable for pre-mixed batches of material or the dispensing device could be a multi-channel volumetric dosing system with static mixing nozzles which can simultaneously mix, dose and dispense silicone material on a continuous basis.

A meniscus 98 is formed when the material 96 is dispensed. FIG. 25B shows that the auto pipette 94 is raised from the platinum silicon pool 96 after dispensing is complete. The meniscus 98 disappears due to reduction of the platinum silicone pool volume with controlled removal, or suck back, of the dispensing device 94. Once the silicone material is set, the exposed surface 104 is partially coated to reduce the "stickiness" of the silicone material by selectively blinding it by printing a pattern of ink or powder onto it, which allows easy removal of the release film when applying the prosthetic.

Figure 26:
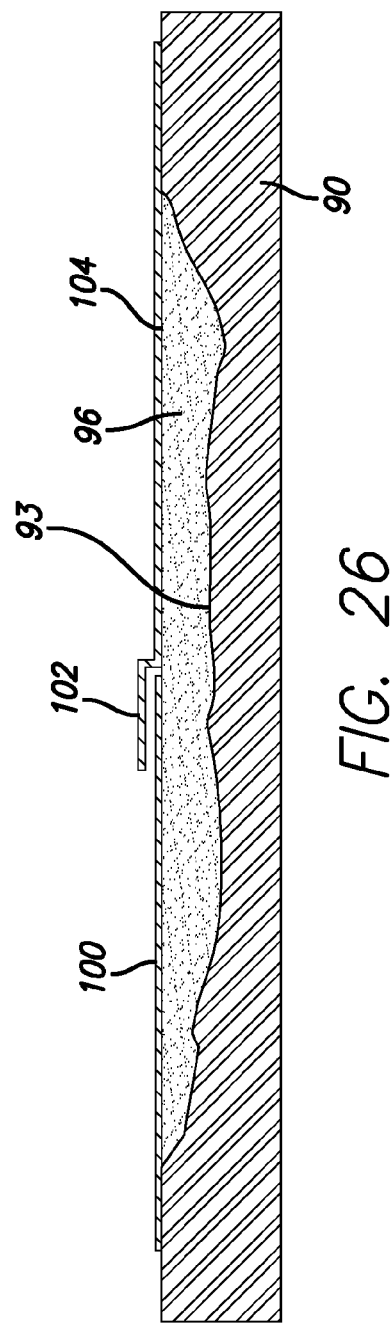
FIG. 26 shows a sectional view of step four for a two layer powder molding process for prosthetics; and, FIG. 27 shows a sectional view of step five for a two layer powder molding process for prosthetics.

Referring now to FIG. 26, two overlapping release films 100 and 102 are applied to the partially coated sticky surface 104 of the prosthetic material. FIG. 27 shows that the two overlapping release films 100 and 102 allow release of the prosthetic 96 which is partially blinded on the exposed outer surface 104 to control the stickiness. The surface of the prosthetic 106 which had been in contact with the impression in the powder bed 90 is coated with powder when it is removed, which completely blinds it, rendering it non-sticky and making it suitable for application without the need for make-up to overcome the natural stickiness of the platinum silicone.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

What is claimed is:

1. A prosthetic appliance comprising layers of a skin safe plastic encapsulation cover, an adhesive layer, a platinum silicone layer, an adhesive layer, a skin safe plastic encapsulation cover layer, a pressure adhesive layer and a release film layer.

2. The prosthetic appliance of claim 1 in which the layers are as follows: the first layer is a skin safe plastic encapsulation cover, the second layer is an adhesive, the third layer is platinum silicone, the fourth layer is an adhesive, the fifth layer is a skin safe plastic encapsulation cover, the sixth layer is a pressure adhesive and the seventh layer is release film.

3. The prosthetic appliance of claim 1 in which the release film is comprised of two pieces of release film, of paper, plastic or metallic foil, in which one piece overlaps the other.

4. The prosthetic appliance of claim 3 in which the release film is coated with cross linkable silicone or a low surface energy material.

5. The prosthetic appliance of claim 1 in which the platinum silicone comprises a softener and a pigment to tint.

6. The prosthetic appliance of claim 5 in which the platinum silicone is softened using a deadener.

7. A prosthetic appliance comprising six layers: skin safe plastic encapsulation cover layer, a platinum silicone layer, an adhesive layer, a skin safe plastic encapsulation cover layer, a pressure adhesive layer and a release film layer.

8. A prosthetic appliance comprising five layers: skin safe plastic encapsulation cover layer, a platinum silicone layer, a skin safe plastic encapsulation cover layer, a pressure adhesive layer and a release film layer.

9. A prosthetic appliance comprising three layers: skin safe plastic encapsulation cover layer, a platinum silicone layer, and a release film layer in which the platinum silicone contains a softener, a pigment to tint and a partial surface coating to reduce stickiness of the silicone material.

* * * * *